US006495602B1

(12) United States Patent
Bhagwat et al.

(10) Patent No.: US 6,495,602 B1
(45) Date of Patent: Dec. 17, 2002

(54) TOPICAL PHARMACEUTICAL BASE WITH ANTI-PRURITIC AND/OR ANTI-INFLAMMATORY DRUGS

(75) Inventors: Dileep Bhagwat, Bronxville, NY (US); Daniel Glassman, Fairfield, NJ (US); Brad P. Glassman, Fairfield, NJ (US)

(73) Assignee: Bradley Pharmaceuticals, Inc., Fairfield, NJ (US)

( * ) Notice: Subject to any disclaimer, the term of this patent is extended or adjusted under 35 U.S.C. 154(b) by 0 days.

(21) Appl. No.: 10/022,132

(22) Filed: Dec. 13, 2001

(51) Int. Cl.[7] .................. A61K 31/17; A61K 7/00; A61K 33/42; A61K 33/06
(52) U.S. Cl. .............. 514/588; 424/401; 424/602; 424/682
(58) Field of Search .................. 514/588; 424/401, 424/602, 682

(56) References Cited

U.S. PATENT DOCUMENTS

| 5,550,112 A | * | 8/1996 | Gallina ................... 514/54 |
| 5,874,074 A | | 2/1999 | Smith ................. 424/78.02 |
| 5,885,597 A | | 3/1999 | Botknecht et al. .......... 424/401 |
| 5,961,997 A | | 10/1999 | Swinehart ................ 424/401 |

OTHER PUBLICATIONS

The Merck Index Tenth Edition 1986 p. 227.*

* cited by examiner

Primary Examiner—Theodore J. Criares
Assistant Examiner—Jennifer Kim
(74) Attorney, Agent, or Firm—Merchant & Gould P.C.

(57) ABSTRACT

Disclosed are compositions of a novel astringent and keratolytic topical pharmaceutical base into which drugs can be incorporated such as for example an anti-pruritic drug and/or an anti-inflammatory drug.

19 Claims, No Drawings

TOPICAL PHARMACEUTICAL BASE WITH ANTI-PRURITIC AND/OR ANTI-INFLAMMATORY DRUGS

FIELD OF INVENTION

The present invention relates to a novel astringent and keratolytic (urea containing) topical pharmaceutical base composition to which other drugs can be added, for example, an anti-pruritic drug like lidocaine, a corticosteroid like hydrocortisone or a combination thereof.

BACKGROUND OF THE INVENTION

Urea has been long recognized as a cosmetic ingredient in formulations acting as a humectant and moisturizer. There have been reports of keratolytic activity attributed to urea with the ability at high concentrations to solubilize and denature protein. High concentrations of urea are also known to have a mild, antimicrobial effect.

Astringents are locally applied compounds which precipitate proteins and shrink mucous membranes. Typically used are aluminum sulfate and calcium acetate. Astringents add significant value to topical cream products and in the healing of damaged skin.

The pH of normal skin is about 4.5–5.5. This acidic pH of the skin provides a natural protection and is referred to as the "Acid Mantle" of the skin. Microorganisms prefer a pH in the range 6–7 to thrive and are therefore held in check by the acidic pH of the skin.

There is a need in the industry for improving on compositions for treating inflamed and pruritic conditions more effectively. A need also exists for a topical pharmaceutical base into which other drugs can be incorporated to provide better efficacy and improved healing of the dermal condition.

SUMMARY OF THE INVENTION

The present invention concerns the finding that the use of topical keratolytics, such as urea, improve drug penetration and the efficacy of traditional anesthetic agents, such as, for example, lidocaine and corticosteroid action.

Accordingly, as one embodiment, the present invention includes a novel topical pharmaceutical base containing astringents and urea which base can be used to incorporate drugs, such as anesthetics and corticosteroids or a mixture thereof. The topical base includes about 1 to about 40 wt % urea; about 0.01 to about 1 wt % of an astringent, and dermatologically acceptable excipients.

The present invention includes as a second embodiment a dermatological composition for treating pruritus conditions containing about 1 to about 40 wt % urea; about 0.01 to about 1 wt % of an astringent; about 0.01 to about 10 wt % of an anesthetic agent, and dermatologically acceptable excipients.

In a third embodiment, the present invention includes a dermatological composition for treating pruritic and inflamed conditions containing about 1 to about 40 wt % urea; about 0.01 to about 1 wt % of an astringent; about 0.01 to about 10 wt % of an anesthetic agent; about 0.001 to about 10 wt % of a corticosteroid, and dermatologically acceptable excipients.

The above dermatological compositions may preferably include one or more non-ionic surfactants. The compositions are preferably creams and have a pH between about 3.0 and 6.5.

DETAILED DESCRIPTION OF THE PREFERRED EMBODIMENT

The present invention first includes a novel pharmaceutical base which drugs can be incorporated into such as anesthetics and corticosteroids or mixtures thereof.

The pharmaceutical base contains urea and an astringent. The urea is contained in an amount from about 1 to about 40 wt % of the total composition. Preferably compositions contain from about 5 to about 35 wt %. The astringent ranges from about 0.01 to about 1 wt % of the composition. Combining astringents and urea in a pharmaceutically acceptable topical base at an acidic pH provides a unique combination of factors for applying topical drugs to the skin and for skin healing.

Astringents precipitate proteins and shrink mucous membrane. Commonly used astringents include salts of cations, including aluminum, zinc, manganese, iron and bismuth; other salts that contain the afore-mentioned metals, such as permanganates; and tannins and related polyphenolic compounds. Examples of specific astringents include aluminum chlorohydrates including hydrate of aluminum chloride hydroxide, aluminum chloride, aluminum sulfate, calcium acetate, zinc sulfate, aluminum ammonium sulfate, aluminum potassium sulfate, aluminum acetate, calamine (iron oxide mixed with zinc oxide), zinc sulfate, zinc caprylate, zinc chloride, zinc oxide, and tannic acid. Preferred astringents include aluminum sulfate, calcium acetate or a mixture thereof.

Examples of drugs incorporated in this topical base include the compositions of the present invention which include about 0.001 to about 10 percent by weight of a corticosteroid, e.g. hydrocortisone or hydrocortisone acetate, or about 0.01 to about 10 percent by weight of an anesthetic agent, e.g. lidocaine or a pharmaceutically acceptable salt thereof. In one embodiment, the weight ratio of anesthetic to corticosteroid is between about 6:1 to about 3:1.

Local anesthetics include, for example, benzocaine, bupivacaine, cocaine, etidocaine, lidocaine, mepivacaine, paroximine, prilocaine, procaine, proparacaine, ropivicaine, and tetracaine.

Corticosteroids include, for example, alclometasone dipropionate, amcinonide, augmented betamethasone dipropionate, beclomethasone dipropionate, betamethasone, betamethasone benzoate, betamethasone dipropionate, betamethasone sodium phosphate, betamethasone valerate, clobetasol propionate, clocortolone pivalate, cortisone, desonide, desoximetasone, dexamethasone, dexamethasone acetate, dexamethasone sodium phosphate, diflorasone acetonide, diflorasone diacetate, fluocinolone acetonide, flucinonide, flunisolide, fluocinolone acetonide, flurandrenolide, fluticasone propionate, halcinonide, halobetasol propionate, hydrocortisone, hydrocortisone acetate, hydrocortisone butyrate, hydrocortisone sodium phosphate, hydrocortisone valerate, methylprednisolone, methylprednisolone acetate, methylprednisolone sodium succinate, mometasone furoate, prednisolone acetate, prednisolone sodium phosphate, prednisolone tebutate, prednisone, triamcinolone, triamcinolone acetonide, triamcinolone diacetate, and triamcinolone hexacetonide. Topical corticosteroids are typically applied as creams, ointments or gels.

Glucocorticoids that are commonly applied topically include betamethasone dipropionate, clobetasol propionate, diflorasone diacetate, halobetasol propionate, amcinodide, flucinonide, halcinonide, betamethasone valerate, diflorasone diacetate, triamcinolone acetonide, flurandrenolide, hydrocortisone valerate, mometasone furoate, hydrocortisone butyrate, aclometasone dipropionate, flucinonolone acetonide, and dexamethasone sodium phosphate.

Preferably, the compositions of the present invention include about 0.01 to about 2.0 percent by weight hydrocortisone and about 1.0 to about 5.0 percent by weight lidocaine and 15 percent urea. In the compositions of the present invention, the ratio of lidocaine to hydrocortisone ranges from about 1.0 to 00.01 to about 5.0 to 2.5. A particularly preferred composition comprises about 3.0 percent by weight lidocaine and about 0.5 percent by weight hydrocortisone with 10 percent urea.

Further, the vehicle used to deliver topical drug products can play an important role in the efficacy and stability of product. This is of particular importance in the development of these formulations.

Generally topical cream formulations are oil in water emulsions (o/w) which allow easy application of the product on the skin without leaving an oily residue. Most o/w cream formulations use anionic surfactants (e.g. sodium lauryl sulfate) in their emulsion system to provide a physically and chemically stable product. Long term stability is an important consideration in the commercialization of a product. Attempts to make formulations with anionic surfactants and lidocaine hydrochloride, caused physical and chemical instability problems. The use of non-ionic surface active agents in the formulations unexpectedly overcome these stability problems and provide an elegant stable topical cream product. The amount of non-ionic surfactant in the above compositions range from about 0.1 to about 10 wt % of the total composition.

Non-ionic surfactants may be relatively water insoluble or quite water soluble.

The water insoluble non-ionic surfactants are the long-chain fatty acids and their water-insoluble derivatives. These include (1) fatty alcohols such as lauryl, cetyl (16 carbons), and stearyl alcohols; (2) glyceryl esters such as the naturally occurring mono-, di-, and triglycerides; and (3) fatty acid esters of fatty alcohols and other alcohols such as propylene glycol, polyethylene glycol, sorbitan, sucrose, and cholesterol. Included also in this general class of nonionic water-insoluble compounds are the free steroidal alcohols such as cholesterol.

To increase the water solubility of these compounds and to form the second group of nonionic agents, polyoxyethylene groups are added through an ether linkage with one of their alcohol groups. The list of derivatives available is much too long to cover completely, but a few general categories will be given.

The most widely used compounds are the polyoxyethylene sorbitan fatty acid esters. Closely related compounds include polyoxyethylene glyceryl, and steroidal esters, as well as the comparable polyoxypropylene esters. It is also possible to have a direct ether linkage with the hydrophobic group as with a polyoxyethylene-stearyl ether or a polyoxyethylene-alkyl phenol. These ethers offer advantages since, unlike the esters, they are quite resistant to acidic or alkaline hydrolysis.

Other suitable combinations from these examples can also be used to serve as the emulsifying system for this invention.

Any dermatologically acceptable carrier can be used in the compositions of the invention. As used herein, "dermatologically acceptable carrier" refers to vehicles, diluents, carriers, which can include adjuvants, additives, or excipients, known for use in dermatological compositions.

The compositions of the invention include, but are not limited to, creams, ointments, solutions, lacquers, sticks, pledgets, wipes, cleansers and/or gels.

The topical composition may be a semi-solid at room temperature but is easily absorbed into the stratum corneum. The semi-solid composition can be a cream. Such a composition can include petroleum-based liquids and solid fractions as skin protectants. The solid skin protectant can be semi-solid. The solid skin protectant can be present in about 5.5% to about 20% in the composition and includes petrolatum or a synthetic or semi-synthetic hydrocarbon of the same nature as petrolatum. Mixtures of such ingredients can also be used. Liquid skin protectants can be petrolatum and contained in the composition in about 10% to about 20% and include any synthetic or semi-synthetic oleaginous liquid fraction. The liquid skin protectant can be mineral oil, which is a liquid mixture of hydrocarbons obtained from petroleum.

The compositions of the invention can include propylene glycol. Propylene glycol can be present in the composition up to about 10%. In one embodiment, propylene glycol is present in the composition at about 1% to about 5%.

The compositions can contain conventional preservatives, such as methyl paraben, propyl and butyl imidazolidinylurea, diazolidinylurea, methylchloroisothiazolinone and methylisothiazolinone. Although not to be held by theory, it is believed that the antimicrobial properties of the urea and antimicrobial agents and propylene glycol allow the composition of the present invention to be free of conventional preservatives.

The present compositions can also contain dermatologically acceptable excipients, such as for example emulsifiers and thickeners. Among these are for example $C_{16}$ to $C_{18}$ straight or branched chain fatty alcohols or fatty acids or mixtures thereof. Examples of emulsifiers and thickeners include cetyl alcohol, stearyl alcohol, stearic acid, palmitic acid, or mixtures thereof. Fatty acids or fatty alcohols may be present in from about 0.25 to 10 wt-%.

Another ingredient useful in the composition of the present invention may be glyceryl stearate, which is a monoester of glycerine and stearic acid, or other suitable forms of glyceryl stearate for example glyceryl stearate SE, which is a commercially available self-emulsifying grade of glycerol stearate that contains some sodium and/or potassium stearate. Glyceryl stearate may be in the composition anywhere from about 1 to about 10% by weight.

The composition can be an emulsion. The emulsion can contain a fatty phase in the range of about 5% to about 60% by weight. Typically, the fatty phase will range from about 5% to about 40% by weight, with respect to the total weight of the composition. Known oils, waxes, emulsifiers and coemulsifiers can be used in compositions in the emulsion form. The emulsifier and the coemulsifier can be present, in the composition, in a proportion ranging from about 0.3% to about 30% by weight. Typically the emulsifier and the coemulsifier are present in a proportion ranging from about 0.5 to about 20% by weight. The emulsion can also contain lipid vesicles.

In one embodiment, the composition can include thickeners which provide a high viscosity cream designed to remain in place upon application to the skin. By way of example, thickeners can include a mixture of a carbomer and triethanolamine. The mixture can be combined together and added to the composition in an amount totaling anywhere from about 0.05 to 30% by weight. Triethanolamine can be purchased as Trolamine NF from BASF. Carbomers come in various molecular weights and are identified by numbers. These are otherwise known as Carbopol. Exemplary Carbopols include is Carbopol 940, 910, 2984, 5984, 954, 980, 981, 941 and 934. Carbopol ETD 2001, 2020, and 2050 and Ultrez 20 are also commercially available and can be used. The carbomer or Carbopols are resins which are known thickening agents. They are homopolymers of acrylic acid crosslinked with an allyl ether of pentaerythritol, an allyl ether of sucrose or an allyl ether of propylene. The carbomer can be present in the composition as a thickener and also can be used to suspend and stabilize the emulsion.

The composition can also contain known adjuvants and additives, such as bactericides, fungicides, virucides, light filter substances, active ingredients with a cooling action, antioxidants, plant extracts, antiinflammatories, substances which promote wound healing, skin-lightening agents, screening agents, odor absorbers, skin-coloring agents, perfumes, antifoams, dyes, pigments which have a coloring action, thickeners, surface-active substances, emulsifiers, emollients, moisturizers and/or humectants, fats, oils, waxes, alcohols, polyols, polymers, foam stabilizers, electrolytes, organic solvents, silicone derivatives or chelating agents. These additives and adjuvants, depending on their nature, can be introduced into the fatty phase, into the aqueous phase and/or into the lipid spherules.

Exemplary oils or waxes suitable for use in the compositions include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Exemplary emulsifiers which are suitable include glyceryl stearate, polysorbate 60, sorbitan monostearate, and the PEG-6/PEG-32/glycol stearate mixture marketed under the trademark Tefose.RTM. 63 by Gattefosse.

Exemplary solvents which can be used in the compositions include the lower alcohols, such as ethanol, isopropanol and propylene glycol.

Exemplary hydrophilic gelling agents suitable for use in the compositions include carboxyvinyl polymers (carbomer), acrylic copolymers such as acrylate/alkyl acrylate copolymers, polyacrylamides, polysaccharides such as hydroxypropylcellulose, natural gums and clays. And exemplary lipophilic gelling agents include modified clays such as bentones, metal salts of fatty acids such as aluminum stearates, and hydrophobic silica, ethylcellulose or polyethylene.

The compositions of the present invention containing drugs may be used in the topical treatment of the following derma, vaginal and anal conditions: pain, itching and irritation, pruritus ani, anal fissures, hemorrhoids, pruritus, insect bites, abrasions, minor bums, pruritus vulvae, pruritic eczemas and similar conditions of the skin and mucous membranes. The compositions of the present invention are particularly useful when these conditions are accompanied by moderate to severe inflammation.

The following Examples give illustrative formulations, of the compositions of the present invention. The following ingredients are combined and packaged by standard techniques, well-known to those skilled in the art. Other topical dosage forms may also be used e.g. Gels, Lotions, solutions, aerosol sprays and the like as required.

EXAMPLE 1

(Astringent with Urea Base Formulation)

Method

1. In a suitable mixing tank (Main Tank) add #2 and heat to about 75° C.
2. Add #3 and #4 and mix to dissolve. Add #1 and mix to dissolve.
3. Add #5, #6 and #7 and continue to mix to dissolve. Maintain temperature at about 75° C.
4. Check pH of Main Tank and adjust the pH to about 4.5, with 10% Sodium Hydroxide Solution (#15). This is the Water Phase.
5. In a second suitable mixing tank add # 8, 9, 10, 11, 12, 13 and 14. Heat to about 75° C. with mixing. This is the Oil Phase.
6. Transfer the Oil Phase (step 5) into the Main Tank (Water Phase) and mix.
7. Cool to about 30° C.
8. Check and adjust the pH to about 4.5 with mixing using #15 if the pH is below 4.5 and #16 if the pH is above 4.5
9. Q.S. the batch to final weight with #17.

EXAMPLE 2

(A Local Anesthetic in an Astringent, Urea Base)

| # | INGREDIENT | % w/w |
|---|---|---|
| 1 | Urea | 10.00 |
| 2 | Purified water | 50.858 |
| 3 | Propylparaben | 0.020 |
| 4 | Methylparaben | 0.200 |
| 5 | Aluminium Sulfate | 0.070 |
| 6 | Calcium Acetate | 0.052 |
| 7 | Glycerin | 8.000 |
| 8 | Light Mineral Oil | 5.000 |
| 9 | White Petrolatum | 5.000 |
| 10 | Stearyl Alcohol | 2.000 |
| 11 | Cetyl Alcohol | 2.000 |
| 12 | Stearic Acid | 5.000 |
| 13 | Sorbitan Monostearate | 1.000 |
| 14 | Polysorbate 60 | 2.000 |
| 15 | Purified Water | 5.000 |
| 16 | Lidocaine Hydrochloride | 3.000 |
| 17 | Sodium Hydroxide 10% | Q.S. |
| 18 | Hydrochloric Acid | Q.S. |
| 19 | Purified Water | Q.S. |

Method

1. In a suitable mixing tank (Main Tank) add #2 and heat to about 75° C.
2. Add #3 and #4 and mix to dissolve. Add #1 and mix to dissolve.
3. Add #5, #6 and #7 and continue to mix to dissolve. Maintain temperature at about 75° C.
4. Check pH of Main Tank and adjust the pH to about 5.0, with 10% Sodium Hydroxide Solution (#17). This is the Water Phase.
5. In a second suitable mixing tank add #8, 9, 10, 11, 12, 13 and 14. Heat to about 75° C. with mixing. This is the Oil Phase.
6. Transfer the Oil Phase (step 5) into the Main Tank (Water Phase) and mix.
7. Cool to about 30° C.
8. In a separate mixing tank dissolve #16 in #15 with mixing and check pH. Adjust pH to about 4.5 with 10% Sodium Hydroxide (#17).
9. Transfer solution from Step 8 into Main Tank and mix.
10. Check and adjust the pH to about 4.5 with mixing using #17 if the pH is below 4.5 and #18 if the pH is above 4.5.
11. Q.S. the batch with #19.

EXAMPLE 3
(A Local Anesthetic & Anti-inflammatory in an Astringent, Urea Base)

| # | INGREDIENT | % w/w |
|---|---|---|
| 1 | Urea | 10.00 |
| 2 | Purified water | 47.958 |
| 3 | Propylparaben | 0.020 |
| 4 | Methylparaben | 0.200 |
| 5 | Aluminum Sulfate | 0.070 |
| 6 | Calcium Acetate | 0.052 |
| 7 | Glycerin | 8.000 |
| 8 | Light Mineral Oil | 5.000 |
| 9 | White Petrolatum | 5.000 |
| 10 | Stearyl Alcohol | 2.000 |
| 11 | Cetyl Alcohol | 2.000 |
| 12 | Stearic Acid | 5.000 |
| 13 | Sorbitan Monostearate | 1.000 |
| 14 | Polysorbate 60 | 2.000 |
| 15 | Hydrocortisone Acetate | 0.500 |
| 16 | Propylene Glycol | 2.400 |
| 17 | Purified Water | 5.000 |
| 18 | Lidocaine Hydrochloride | 3.200 |
| 19 | Sodium Hydroxide 10% | Q.S. |
| 20 | Hydrochloric Acid | Q.S. |
| 21 | Purified Water | Q.S. |

Method

1. In a suitable mixing tank (Main Tank) add #2 and heat to about 75° C.

2. Add #3 and #4 to the Main Tank and mix to dissolve. Add #1 and mix to dissolve.

3. Add #5 and #6 and #7 to the Main Tank continue to mix to dissolve. Maintain temperature at about 75° C. This is the Water Phase 4. Check the pH of the Main Tank and adjust to about 5.0 with #19. This is the Water Phase.

5. In a second suitable mixing tank add ingredients #'s 8, 9, 10, 11, 12 13 and 14. Heat to about 75° C. with mixing. This is the Oil Phase.

6. Transfer the Oil Phase (step 5) into the Main Tank (Water Phase) and mix.

7. In a separate mixing tank dispense #15 in #16 with mixing.

8. Add the dispersion from Step 7 into the Main Tank and continue to mix and cool to about 30° C.

9. In a separate mixing tank, place ingredient #17 and add #18. Mix to dissolve. Transfer to Main Tank and continue to mix.

10. Check pH of the Main Tank and adjust to about 4.5 with 10% Sodium Hydroxide Solution.

11. If the pH is above 4.5 adjust with #20 to about 4.5.

12. Add Purified Water to Q.S. the batch to final weight.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A composition comprising:
    (a) about 1 to about 40 wt. % urea;
    (b) about 0.01 to about 1 wt % of an astringent selected from the group consisting of calcium acetate, aluminum sulfate, or a mixture thereof; and dermatologically acceptable excipients.

2. The composition of claim 1 in the form of a topical cream.

3. The composition of claim 1, having a pH between about 3.0 and 6.5

4. A dermatological composition comprising:
    (a) about 1 to about 40 wt % urea;
    (b) about 0.01 to about 1 wt % of an astringent selected from the group consisting of calcium acetate, aluminum sulfate, or a mixture thereof;
    (c) about 0.01 to about 10 wt % of an anesthetic agent, and dermatologically acceptable excipients.

5. The composition of claim 4, wherein the anesthetic agent is lidocaine or a pharmaceutically acceptable salt thereof.

6. The composition of claim 4, in the form of a topical cream.

7. The composition of claim 4, having a pH between about 3.0 and 6.5.

8. The composition of claim 4, which further comprises from about 0.1 to about 10 wt % of a non-ionic surfactant.

9. The composition of claim 8, where the non-ionic surfactant is selected from fatty alcohols, glyceryl esters, fatty acid esters of fatty alcohols and mixtures thereof.

10. The composition of claim 8, where the non-ionic surfactant is a polyoxyethylene sorbitan fatty acid ester or mixtures thereof.

11. A dermatological composition comprising:
    (a) about 1 to about 40 wt % urea;
    (b) about 0.01 to about 1 wt % of an astringent selected from the group consisting of calcium acetate, aluminum sulfate or a mixture thereof; (c) about 0.01 to about 10 wt % of an anesthetic agent;
    (d) about 0.001 to about 10 wt % of a corticosteroid, and dermatologically acceptable excipients.

12. The composition of claim 11, where the weight ratio of anesthetic agent to corticosteroid is between about 6:1 to about 3:1.

13. The composition of claim 11, wherein the anesthetic agent is lidocaine or a pharmaceutically acceptable salt thereof.

14. The composition of claim 11, wherein the corticosteroid is hydrocortisone or hydrocortisone acetate.

15. The composition of claim 11, which further comprises from about 0.1 to about 10 wt % of a non-ionic surfactant.

16. The composition of claim 15, where the non-ionic surfactant is selected from fatty alcohols, glyceryl esters of fatty alcohols, fatty acid esters of fatty alcohols, and mixtures thereof.

17. The composition of claim 15, where the non-ionic surfactant is a polyoxyethylene sorbitan fatty acid ester or a mixture thereof.

18. The composition of claim 11, in the form of a topical cream.

19. The composition of claim 11, having a pH between about 3.0 and about 6.5.

* * * * *

UNITED STATES PATENT AND TRADEMARK OFFICE
CERTIFICATE OF CORRECTION

PATENT NO. : 6,495,602 B1
DATED : December 17, 2002
INVENTOR(S) : Bhagwat et al.

It is certified that error appears in the above-identified patent and that said Letters Patent is hereby corrected as shown below:

<u>Title page,</u>
Item [75], Inventors, "Brad P. Glassman" should read -- Bradley P. Glassman --

<u>Column 5,</u>
Line 57, "minor bums," should read -- minor burns, --

<u>Column 6,</u>
Line 3, Under EXAMPLE 1 (Astringent with Urea Base Formulation) insert Table

| # | INGREDIENT | %w/w |
|---|---|---|
| 1 | Urea | 10.00 |
| 2 | Purified water | 60.858 |
| 3 | Propylparaben | 0.020 |
| 4 | Methylparaben | 0.200 |
| 5 | Aluminium Sulfate | 0.070 |
| 6 | Calcium Acetate | 0.052 |
| 7 | Glycerin | 8.000 |
| 8 | Light Mineral Oil | 5.000 |
| 9 | White Petrolatum | 5.000 |
| 10 | Stearyl Alcohol | 2.000 |
| 11 | Cetyl Alcohol | 2.000 |
| 12 | Stearic Acid | 5.000 |
| 13 | Sorbitan Monostearate | 1.000 |
| 14 | Polysorbate 60 | 2.000 |
| 15 | Sodium Hydroxide 10% | Q.S. |
| 16 | Hydrochloric Acid | Q.S. |
| 17 | Purified Water | Q.S. |

Signed and Sealed this

Fifteenth Day of July, 2003

JAMES E. ROGAN
*Director of the United States Patent and Trademark Office*